(12) United States Patent
Elsik

(10) Patent No.: US 8,435,927 B2
(45) Date of Patent: May 7, 2013

(54) HIGH-LOAD GLYPHOSATE FORMULATIONS

(75) Inventor: Curtis M. Elsik, The Woodlands, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 757 days.

(21) Appl. No.: 11/664,457

(22) PCT Filed: Sep. 29, 2005

(86) PCT No.: PCT/US2005/034958
§ 371 (c)(1),
(2), (4) Date: Oct. 28, 2008

(87) PCT Pub. No.: WO2006/041702
PCT Pub. Date: Apr. 20, 2006

(65) Prior Publication Data
US 2009/0215626 A1    Aug. 27, 2009

Related U.S. Application Data

(60) Provisional application No. 60/615,705, filed on Oct. 4, 2004.

(51) Int. Cl.
*A01N 57/00* (2006.01)
(52) U.S. Cl.
USPC .......................................... 504/127; 504/206

(58) Field of Classification Search ........................ None
See application file for complete search history.

(56) References Cited

U.S. PATENT DOCUMENTS

| | | | |
|---|---|---|---|
| 5,668,085 A | 9/1997 | Forbes et al. | |
| 6,248,695 B1 * | 6/2001 | Griffiths et al. | 504/206 |
| 6,992,045 B2 * | 1/2006 | Xu et al. | 504/206 |
| 2002/0123430 A1 * | 9/2002 | Xu et al. | 504/206 |
| 2004/0142823 A1 * | 7/2004 | Elsik et al. | 504/365 |

FOREIGN PATENT DOCUMENTS

| | | |
|---|---|---|
| EP | 0999749 B1 | 5/2000 |
| EP | 1133233 B1 | 9/2001 |
| EP | 1438896 A1 | 7/2004 |
| WO | WO 0030451 | 6/2000 |

* cited by examiner

*Primary Examiner* — Alton Pryor
(74) *Attorney, Agent, or Firm* — Huntsman International LLC

(57) ABSTRACT

By the present invention, a surfactant system containing glyphosate has been created which can be used to yield formulations containing an ultra-high load of glyphosate, in which the glyphosate concentration is higher than previously possible in any agriculturally-acceptable formulation. Higher loadings are desirable to reduce shipping and container costs, as well as reduce wastes. The higher loading reduces storage requirements and allows the farmer to handle less volume of pesticide. The main advantage is that maximizing the loading minimizes the cost to deliver the active ingredient, which in turn maximizes economy in use of glyphosate.

28 Claims, 4 Drawing Sheets

HIGH-LOAD GLYPHOSATE FORMULATIONS

Cross Reference to Related Applications

This application is the National Phase of International Application PCT/US2005/034958 filed Sep. 29, 2005 which designated the U.S. and which claims priority to U.S. Pat. App. Ser. No. 60/615,705 filed Oct. 4, 2004. The noted applications are incorporated herein by reference.

FIELD OF THE INVENTION

The present invention relates generally to pesticide products formulated as aqueous solutions. More particularly, it relates to aqueous compositions which contain the herbicide N-phosphonomethyl glycine ("glyphosate") in the form of a salt other than its potassium salt, and preferably its mono-iso-propylamine salt.

BACKGROUND INFORMATION

The present invention pertains to liquid compositions of matter useful as herbicides and to liquid concentrates from which liquid herbicides may be prepared, wherein the active herbicidal ingredient is a salt of N-phosphonomethyl glycine, which is commonly referred to as glyphosate by those skilled in this art. Owing to the fact that glyphosate in its acid form has a low solubility in water, those skilled in the art who produce and/or use formulations containing glyphosate have found it beneficial to employ a water-soluble glyphosate salt in their formulations in order to achieve higher levels of glyphosate effectively dissolved in the solutions. This is regarded as being common knowledge in the art, and salts typically employed are the amine salts of glyphosate, including without limitation the mono-iso-propylamine salt of glyphosate, alkanolamine salts of glyphosate, the alkali and/or alkaline earth metal salts of glyphosate, and mixtures comprising any of the foregoing.

In a general sense, it is desirable to provide concentrates which contain one or more salts of glyphosate in as high a concentration as possible because the higher the concentration, the more active ingredient is contained in a given volume, which reduces shipping costs and enables large volumes of final solutions to be prepared from small volumes of concentrate by mere addition of water. Thus, it is desirable to increase the maximum level of glyphosate loading possible to successfully formulate in a commercially-viable product.

One current commercial glyphosate formulation is the mono-iso-propylamine ("IPA") salt in loaded at 480 g/L active ingredient, which is approximately 360 g/L glyphosate (acid form) equivalent. U.S. Pat. No. 5,668,085 discloses that mono-iso-propylamine glyphosate solutions are easily prepared containing 250-400 g/L of glyphosate acid equivalent.

European Patent EP 1 133 233 B1 (WO 00030452 A1) discloses an adjuvant system compatible with the mono-ethanolamine ("MEA") salt of glyphosate. Table 1 of this patent shows how the cloud point decreases with increasing surfactant concentration. The patent further states the commonly-held belief that to maintain acceptable cloud point when raising the concentration of glyphosate, the surfactant concentration must be reduced. The cloud point is a measure of the maximum temperature at which a given aqueous composition containing a surfactant and a salt of glyphosate at defined concentrations forms a single-phase solution. Above the cloud point, the surfactant separates from the solution, initially as a hazy or cloudy dispersion, and, upon standing, as a distinct phase generally rising to the surface of the solution. (Cloud point of a composition is normally determined by heating the composition until the solution becomes cloudy, and then allowing the composition to cool, with agitation, while its temperature is continuously monitored. A temperature reading taken when the solution clears is a measure of cloud point.) European Patent EP 0 999 749 B1 discloses high-load ammonium glyphosate. The publications WO 00/30451 and EP1438896A1 disclose compositions containing the MEA salt of glyphosate.

The object of this invention is to provide commercially viable products of very high loaded glyphosate formulations. This invention pertains to IPA salts of glyphosate.

BRIEF DESCRIPTION OF THE DRAWINGS

In the annexed drawings.

SUMMARY OF THE INVENTION

Figure 1:
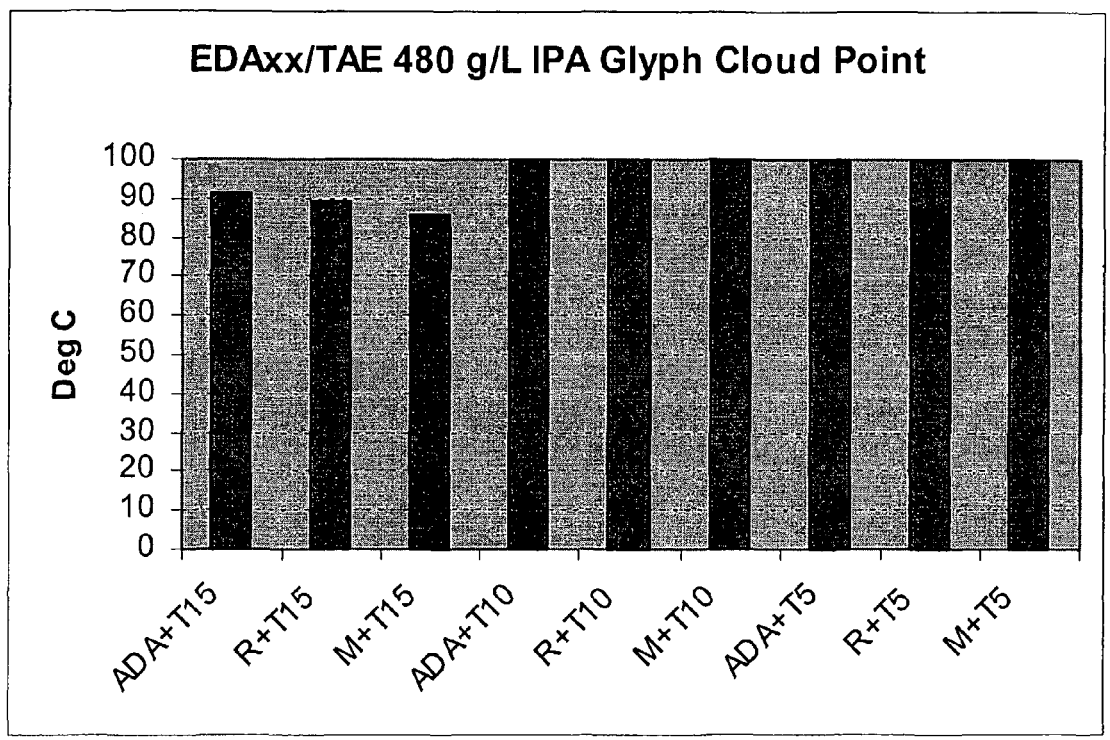
FIG. 1 graphically depicts the cloud points of solutions containing the mono-iso-propylamine salt and various surfactants and surfactant combinations at a glyphosate loading of 480 grams per liter.

The present invention provides liquid compositions of matter comprising: a) a glyphosate salt in an amount greater than 480 g/L a.i.; b) a tallowamine alkoxylate; and c) an EDA alkoxylate.

In another embodiment, the present invention provides liquid compositions of matter comprising: a) a glyphosate salt in an amount greater than 580 g/L a.i.; b) a tallowamine alkoxylate; and c) an EDA alkoxylate, wherein the composition has a cloud point greater than 90° C.

DETAILED DESCRIPTION OF THE INVENTION

The present disclosure specifies the creation of mixtures comprising ethylenediamine alkoxylates and tallowamine ethoxylates which form stable, homogeneous solutions in combination with the mono-iso-propylamine salt of glyphosate at higher loadings of the glyphosate salt. Example formulations have been made at both 430 g/L glyphosate acid equivalent ("ae") and 505 g/L glyphosate acid equivalent. The 505 g/L ae formulation enabled observation of two unexpected properties: 1) the cloud point actually increased as the level of glyphosate loading was raised; and 2) a high level of surfactant was maintained at the high glyphosate loading.

According to the work carried out in connection with the present specification, surfactant blends were made using alkoxylates of ethylene diamine ("alkoxylated EDA") and alkoxylates of tallowamine ("alkoxylated tallowamine"), including those which now follow. The surfactant sold as SURFONIC® ADA-170 surfactant is an alkoxylated ethylenediamine ("EDA"), (propylene oxide ("PO")/ethylene oxide ("EO") block) surfactant, and is available from Huntsman LLC of Houston, Tex. The surfactant sold as SURFONIC® R-170 surfactant is an alkoxylated EDA (EO/PO block) surfactant that is also available from Huntsman LLC of Houston, Tex. The surfactant known as SURFONIC® M-170 surfactant is an alkoxylated EDA (EO/PO mixed block) surfactant is also available from Huntsman LLC of Houston, Tex. The surfactant known as SURFONIC® T-15 surfactant is a 15-mole alkoxylated tallowamine (ethylene oxide) that is available from Huntsman LLC. The surfactant known as SURFONIC® T-5 surfactant is a 5-mole alkoxylated tallowamine (ethylene oxide) that is available from Huntsman LLC. The surfactant known as SURFONIC® T-10 surfactant is a 10-mole alkoxylated tallowamine (ethylene oxide) that is available from Huntsman LLC. The glycol sold as POGOL® 400 PEG is a polyethylene glycol with an average molecular weight of about 400 that is also available from Huntsman LLC of Houston, Tex.

It is convenient for this specification and FIGS. 1-4 that the foregoing surfactants be abbreviated as set forth in table I below:

TABLE I abbreviations

| Surfactant Name | Abbreviation |
|---|---|
| SURFONIC ® ADA-170 | ADA |
| SURFONIC ® R-170 | R |
| SURFONIC ® T-15 | T15 |
| SURFONIC ® T-10 | T10 |
| SURFONIC ® T-5 | T5 |
| SURFONIC ® M-170 | M |

Nine adjuvant compositions were prepared using the formula in the table II below:

TABLE II formula for adjuvants

| Component | w/w % |
|---|---|
| EDA Alkoxylate | 40 |
| Tallowamine ethoxylate | 40 |
| POGOL ® 400 PEG | 10 |
| H$_2$O | 10 |
| Total | 100 | using the three alkoxylated EDA surfactants and the three alkoxylated tallowamine surfactants mentioned above in the combinations specified in Table III below:

TABLE III surfactants used in adjuvants

| Adjuvant Number | Specific Surfactants Used |
|---|---|
| 1 | ADA + T15 |
| 2 | R + T15 |
| 3 | M + T15 |
| 4 | ADA + T10 |
| 5 | R + T10 |
| 6 | M + T10 |
| 7 | ADA + T5 |
| 8 | R + T5 |
| 9 | M + T5 | using the mono-iso-propylamine salt of glyphosate ("IPA glyphosate") in formulations at three loadings according to table IV below, in which quantities of ingredients are specified in parts by weight:

TABLE IV compositions of finished concentrates

| Component | Normal Load | High Load | Very High Load |
|---|---|---|---|
| IPA glyphosate (62% a.i.) | 66.1 | 78.5 | 90.0 |
| adjuvant blend | 7.5 | 7.5 | 10.0 |
| Water | 26.4 | 14.0 | — |
| Total: | 100 | 100 | 100 |
| g/L a.i. (active ingr.) | 480 | 580 | 680 |
| g/L ae (acid equiv) | 360 | 430 | 505 |
| S.G. (25/4) | 1.17 | 1.20 | 1.22 |

Figure 2:
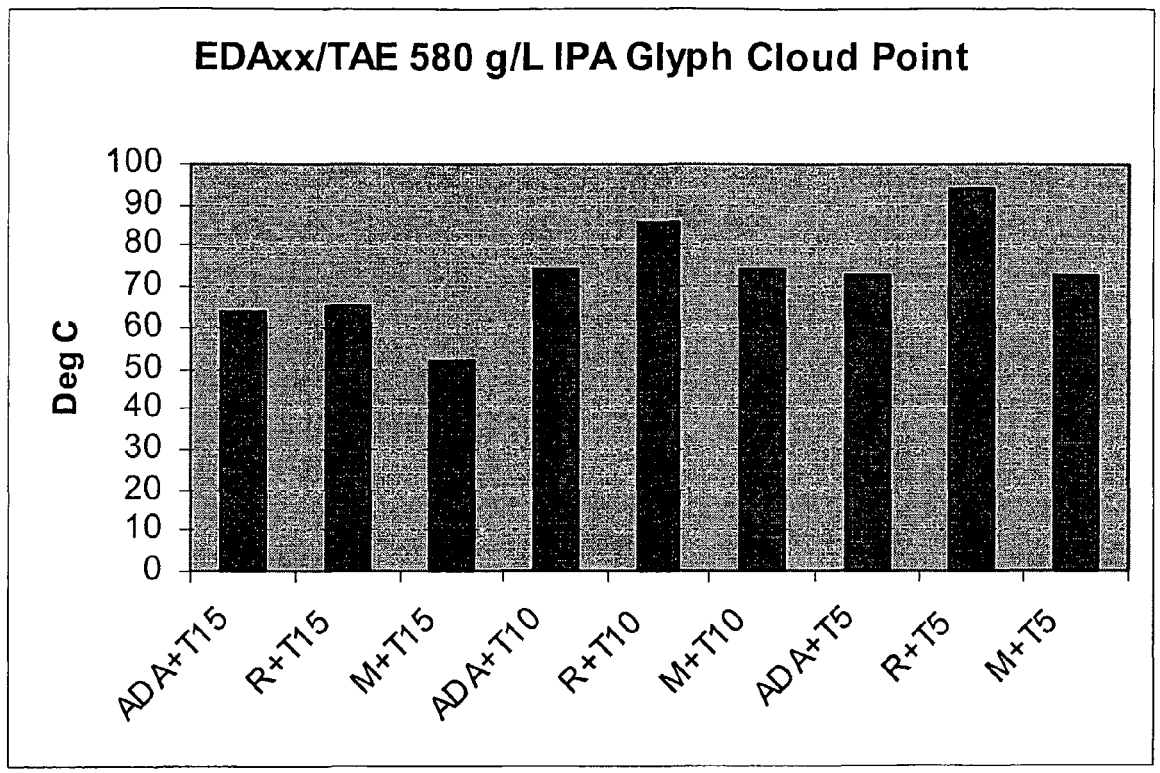
FIG. 2 graphically depicts the cloud points of solutions containing the mono-iso-propylamine salt and various surfactants and surfactant combinations at a glyphosate loading of 580 grams per liter.
Figure 3:
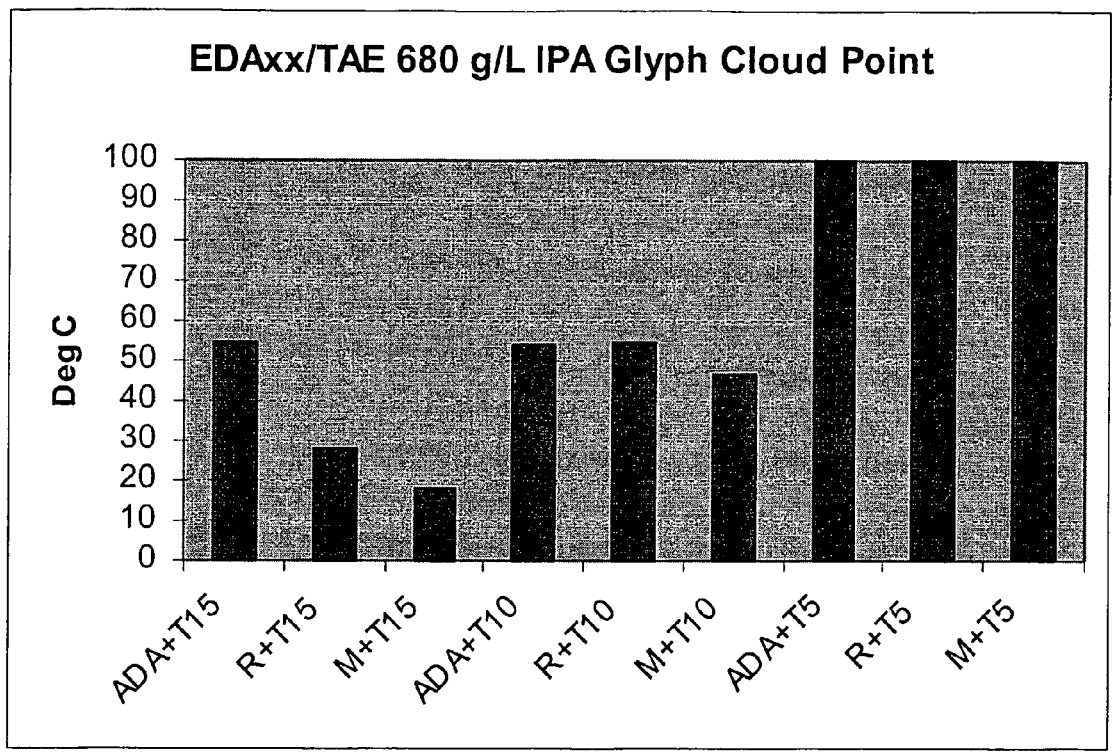
FIG. 3 graphically depicts the cloud points of solutions containing the mono-iso-propylamine salt and various surfactants and surfactant combinations at a glyphosate loading of 680 grams per liter.

Cloud point tests were run on the twenty-seven glyphosate formulations so produced using the nine adjuvant formulations for each level of loading specified in table IV, and the results are depicted graphically in FIGS. 1-3. The cloud point was determined by a three-step procedure of: 1) heating the solution until it becomes cloudy and thence removing the heat source; 2) mechanically stirring the cloudy solution while monitoring its temperature as the sample cools; and 3) recording the temperature at the point at which the solution displays complete clarity. Those of ordinary skill in the art immediately recognize that a cloud point equal or greater than 50° C. is generally required in order for a composition to possess the status of being commercially acceptable.

TABLE V cloud point results for finished concentrates

| | IPA glyphosate loading g/L a.i. | | |
|---|---|---|---|
| | 480 | 580 | 680 |
| Adjuvant number | cloud point (° C.) | | |
| 1 | 91 | 64 | 55 |
| 2 | 89 | 65 | 28 |
| 3 | 86 | 52 | 18 |
| 4 | >100 | 74 | 54 |
| 5 | >100 | 86 | 55 |
| 6 | >100 | 74 | 47 |
| 7 | >100 | 73 | >100 |
| 8 | >100 | 94 | >100 |
| 9 | >100 | 73 | >100 |

Figure 4:
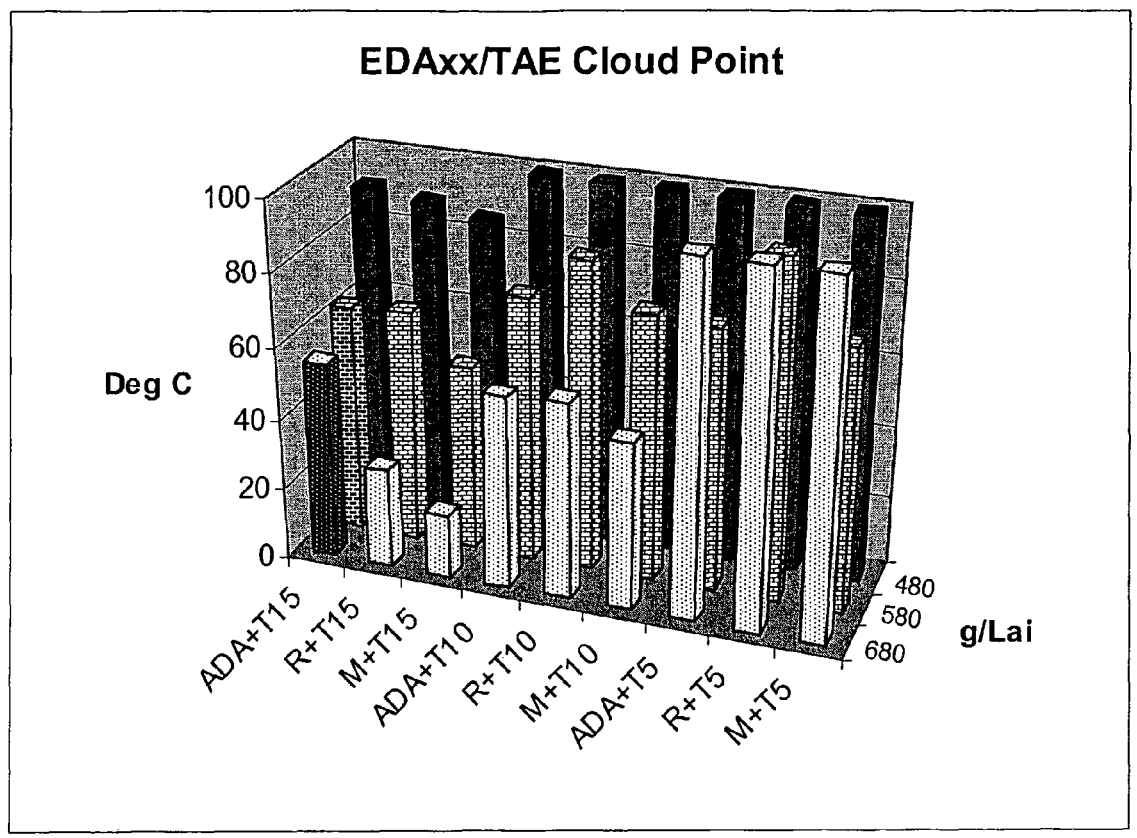
FIG. 4 comprises the graphs from FIGS. 1-3 on the same graph.

These data are plotted individually in FIGS. 1-3, and combined in FIG. 4. All of the 480 and 580 g/L a.i. formulations are homogeneous and have a cloud point greater than 50° C.

The data in Table V and the FIGS. 1-3 show the known trend of increasing cloud point with decreasing moles of ethylene oxide present on the ethoxylated tallowamine surfactant.

However, the compositions according to this invention display results which are wholly unexpected. Firstly, the cloud point increased as the loading was increased from 580 to 680 g/L a.i. IPA glyphosate for the EDA/T-5 adjuvant formulations (adjuvants 7, 8, 9). This is in direct opposition to what one of ordinary skill in the art would expect, as the cloud point normally decreases as glyphosate loading is increased.

Secondly, the cloud point increased as the surfactant concentration was increased. The 580 g/L a.i. formulation contains 7.5 w/w % adjuvant and the 680 g/L a.i. formulation contains 10.0 w/w % adjuvant. This is in direct opposition to what one of ordinary skill in the art would expect, as the cloud point normally decreases as surfactant loading is increased.

Thus, by the present invention, a surfactant system containing IPA glyphosate has been created which can be used to yield formulations containing an ultra-high load of IPA glyphosate, in which the IPA glyphosate concentration is higher than previously possible in any agriculturally-acceptable formulation. With the combinations made using adjuvants numbers 7, 8, and 9, cloud point increased with increased IPA glyphosate loading, instead of trending downward as one of ordinary skill would expect. Thus, according to the present invention, surfactant loading is increased and maintained at the highest IPA glyphosate loading without adversely affecting cloud point.

The three formulations with EDA/T-5 blends (adjuvant numbers 7, 8, 9) were stored for one week at 5° C. in order to determine low-temperature stability. After the expiry of 7 days under such conditions, there was no crystallization present and the solutions had remained homogeneous. Thus, the present invention has provided low temperature-stable, homogeneous formulations of very highly loaded IPA glyphosate, using a range of surfactant blends. The adjuvant chemistry of this invention allows the successful formulation of very high loadings using the IPA salt of glyphosate.

The tallowamine ethoxylate used in the practice of this invention according to one of its preferred forms is a mixture of materials having the general structure:

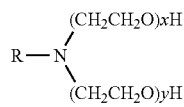

wherein R is a mixture of hydrocarbon groups typical of tallow as are well known in the art to comprise alkyl and alkenyl groups having between about 12 and 20 carbon atoms, is mostly $C_{18}$, and in which x and y are each independently any value within the range of between about 1 and about 12, with a value for x and y each of about 2-3 being most preferable.

The alkoxylated EDA component (ADA-170) of a composition according to the invention is a mixture of materials conforming to the general structure:

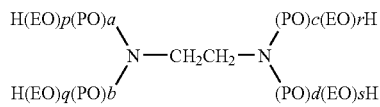

wherein EO and PO represent ethylene oxide and propylene oxide units, respectively, and in which a, b, c, d may each independently be any value between about 0 and 3, including 0 and 3, the sum of a+b+c+d has a preferred average value of about 4, but the sum of a+b+c+d may be any value in the range of between about 2 and 8, and in which the sum of p+q+r+s has a preferred average value of about 22 but the average sum of p+q+r+s may be any value in the range of between about 16 and 30.

The alkoxylated EDA component (R-170) of a composition according to another embodiment of the invention is a mixture of materials conforming to the general structure:

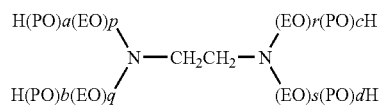

wherein EO and PO represent ethylene oxide and propylene oxide units, respectively, and in which a, b, c, d may each independently be any value between about 0 and 3, including 0 and 3, the sum of a+b+c+d has a preferred average value of about 4, but the sum of a+b+c+d may be any value in the range of between about 2 and 8, and in which the sum of p+q+r+s has a preferred average value of about 22 but the average sum of p+q+r+s may be any value in the range of between about 16 and 30.

The alkoxylated EDA component (M-170) of a composition according to one embodiment of the invention is a mixture of materials conforming to the general structure:

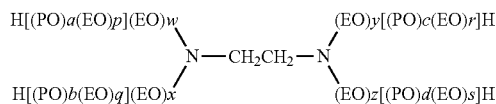

wherein EO and PO represent ethylene oxide and propylene oxide units, respectively, and in which w, x, y, and z in each occurrence may each independently be any integer between about 0 and 3, including 0 and 3 such that the sum of w+x+y+z is any value in the range of between about 2 and 8; and in which p, q, r, and s in each occurrence may independently be any integer between about 0 and 10, including 0 and 10 such that the sum of p+q+r+s is any value in the range of between about 12 and 24; and in which a, b, c, and d in each occurrence may independently be any integer between about 0 and 3, including 0 and 3 such that the sum of a+b+c+d is any value in the range of about 2 to 8, subject to the proviso that the EO/PO units within the [square brackets] in this equation are added in a random fashion to the EO already connected to the nitrogen atoms, that is, the material is formed by reacting a mixture of the gases EO and PO are with a precursor, which precursor already contains EO attached to the nitrogen atoms in ethylene diamine in an amount as defined by x above.

Thus, the present invention comprises mixtures of two or more alkoxylated nitrogenous substances. It is recognized by those skilled in the art that during the alkoxylation process the alkylene oxide units may add to the nitrogenous substance being alkoxylated in either a random or block fashion. Thus, the compositions of the invention shall not be construed as being limited to any specific structure with regards to which the EO and PO units are present in the molecules, except as otherwise specified herein. It is also recognized that during such alkoxylations used to provide the alkoxylated materials used as components in this invention that a mixture of products are obtained; hence the values of x, y, and z as they represent alkoxide units are average values, as specified.

The present invention also includes compositions containing the molecules as expressed herein in which the propylene oxide is replaced by butylene oxide. The tallowamine may also include propylene oxide units and butylene oxide units.

The present invention also comprises a process for controlling weeds which comprises the step of applying a composition according to the invention to soil and/or foliage. The present invention also comprises a process for controlling weeds which comprises the steps of: 1) diluting any composition according to the invention with any desired amount of water and applying any composition according to the invention to soil and/or foliage.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. The present disclosure includes the subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claim so modified. This also includes combination of the features and/or limitations of one or more of the independent claims with the features and/or limitations of another independent claim to arrive at a modified independent claim, with the remaining dependent claims in their original text being read and applied to any independent claim so modified. Accordingly, the presently disclosed invention is intended to cover all such modifications and alterations, and is limited only by the scope of the claims which follow, in view of the foregoing and other contents of this specification.

What is claimed is:

1. A liquid composition of matter comprising:
a) a glyphosate salt in an amount greater than 580 g/L a.i.;
b) a tallowamine alkoxylate comprising a mixture of materials represented by the formula:

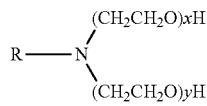

in which R is selected from the group consisting of: alkyl and alkenyl groups having between about 12 and 20 carbon atoms, and in which x and y are each independently any value within the range of between about 1 and about 12; and
c) an ethylenediamine (EDA) alkoxylate comprising a mixture of materials conforming to the general structure:

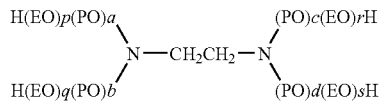

wherein EO and PO represent ethylene oxide and propylene oxide units, respectively, and in which each of a, b, c, d in each occurrence are independently any value between about 0 and about 3, including 0 and about 3, wherein the sum of a+b+c+d is any value in the range of between about 2 and about 12, and in which the sum of p+q+r+s is any value in the range of between about 16 and 30, wherein the composition has a cloud point greater than 60° C., wherein said glyphosate salt comprises the mono-iso-propylamine salt of N-phosphonomethyl glycine.

2. A composition according to claim 1 wherein the sum of a+b+c+d is about 4 and wherein the sum of p+q+r+s is about 22.

3. A composition according to claim 1 wherein said glyphosate salt is present in an amount greater than 600 g/L a.i.

4. A composition according to claim 1 in which the cloud point is at least 70° C.

5. A composition according to claim 1 in which the cloud point is at least 80° C.

6. A composition according to claim 1 in which the cloud point is at least 90° C.

7. A composition according to claim 1 in which the cloud point is at least 95° C.

8. A liquid composition of matter comprising:
a) a glyphosate salt in an amount greater than 580 g/L a.i.;
b) a tallowamine alkoxylate comprising a mixture of materials represented by the formula:

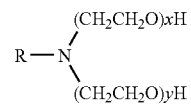

in which R is selected from the group consisting of: alkyl and alkenyl groups having between about 12 and 20 carbon atoms, and in which x and y are each independently any value within the range of between about 1 and about 12; and
c) an ethylenediamine (EDA) alkoxylate comprising a mixture of materials conforming to the general structure:

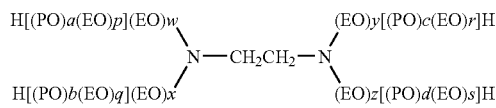

wherein each of EO and PO represent ethylene oxide and propylene oxide units, respectively, and in which each of w, x, y, and z in each occurrence is independently any integer between about 0 and about 3, including 0 and about 3, such that the sum of w+x+y+z is any value in the range of between about 2 and about 12; and in which each of p, q, r, and s in each occurrence is independently any integer between about 0 and about 10, including 0 and about 10 such that the sum of p+q+r+s is any value in the range of between about 12 and about 24; and in which a, b, c, and d in each occurrence may independently be any integer between about 0 and 3, including 0 and 3 such that the sum of a+b+c+d is any value in the range of about 2 to 7, subject to the proviso that the EO/PO units within the [square brackets] in this equation are added in a random fashion to the EO already attached to the nitrogen atoms and described by w, x, y, and z, wherein said glyphosate salt comprises the mono-iso-propylamine salt of N-phosphonomethyl glycine.

9. A composition according to claim 8 wherein said glyphosate salt is present in an amount greater than 600 g/L a.i.

10. A liquid composition of matter comprising:
a) a glyphosate salt present in any amount between about 470 g/L and about 680 g/L, calculated as the acid form of glyphosate;
b) a tallowamine alkoxylate comprising a mixture of materials represented by the formula:

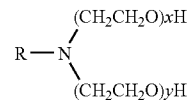

in which R is selected from the group consisting of: alkyl and alkenyl groups having between about 12 and 20 carbon atoms, and in which x and y are each independently any value within the range of between about 1 and about 12; and c) a polyamine alkoxylate, wherein the structure of the polyamine alkoxylate comprises two nitrogen atoms and includes at least two different alkylene oxide units selected from the group consisting of: ethylene oxide (EO), propylene oxide (PO), and butylene oxide (BO), in which the ratio of the amount of the lower molecular weight alkylene oxide present in the molecule to the amount of the higher molecular weight alkylene oxide present in the molecule is in the range of between about 6:1 to 3:1, wherein the composition has a cloud point greater than 60° C, wherein said glyphosate salt comprises the mono-iso-propylamine salt of N-phosphonomethyl glycine.

11. A composition according to claim 10 wherein said polyamine alkoxylate comprises EO units and PO units.

12. A composition according to claim 11 wherein the ratio of the amount of EO present in the polyamine alkoxylate to the amount of PO present in the polyamine alkoxylate is at least 3:1.

13. A composition according to claim 11 wherein the ratio of the amount of EO present in the polyamine alkoxylate to the amount of PO present in the polyamine alkoxylate is at least 4:1.

14. A composition according to claim 11 wherein the ratio of the amount of EO present in the polyamine alkoxylate to the amount of PO present in the polyamine alkoxylate is at least 5:1.

15. A composition according to claim 10 in which the cloud point is at least 70° C.

16. A composition according to claim 10 in which the cloud point is at least 80° C.

17. A composition according to claim 10 in which the cloud point is at least 90° C.

18. A composition according to claim 10 in which the cloud point is at least 95° C.

19. A composition according to claim 10 which is substantially free from potassium.

20. A composition according to claim 10 in which said glyphosate salt is present in an amount of at least 490 grams per liter, calculated as the acid form of glyphosate.

21. A composition according to claim 10 in which said glyphosate salt is present in an amount of at least 520 grams per liter, calculated as the acid form of glyphosate.

22. A composition according to claim 10 in which said glyphosate salt is present in an amount of at least 550 grams per liter, calculated as the acid form of glyphosate.

23. A composition according to claim 10 in which said glyphosate salt is present in an amount of at least 580 grams per liter, calculated as the acid form of glyphosate.

24. A composition according to claim 10 in which said glyphosate salt is present in an amount of at least 610 grams per liter, calculated as the acid form of glyphosate.

25. A composition according to claim 10 in which said glyphosate salt is present in an amount of at least 640 grams per liter, calculated as the acid form of glyphosate.

26. A composition according to claim 10 in which said glyphosate salt is present in an amount of at least 670 grams per liter, calculated as the acid form of glyphosate.

27. A liquid composition of matter comprising:
a) a glyphosate salt in an amount greater than 580 g/L a.i.
b) a mono-amine alkoxylate selected from ethoxylates, propoxylates and butoxylates, wherein said alkoxylate contains any number of alkylene oxide units between about 1 and 12; and
c) a polyamine alkoxylate, wherein the polyamine alkoxylate comprises two nitrogen atoms and includes at least two different alkylene oxide units selected from the group consisting of: ethylene oxide, propylene oxide, and butylene oxide in which the ratio of the amount of the lower molecular weight alkylene oxide present in the molecule to the amount of the higher molecular weight alkylene oxide present in the molecule is in the range of between about 6:1 to 3:1, wherein said glyphosate salt comprises the mono-iso-propylamine salt of N-phosphonomethyl glycine.

28. A liquid composition of matter comprising:
a) a glyphosate salt in an amount greater than 580 g/L a.i.;
b) a mono-amine alkoxylate selected from ethoxylates, propoxylates and butoxylates, wherein the nitrogen atom of said alkoxylate has two groups or chains of alkylene oxide units attached to it, each of which groups or chains contain any number of alkylene oxide units between about 1 and 12; and
c) a polyamine alkoxylate, wherein the structure of the polyamine alkoxylate comprises two nitrogen atoms and includes at least two different alkylene oxide units selected from the group consisting of: ethylene oxide, propylene oxide, and butylene oxide, in which the ratio of the amount of the lower molecular weight alkylene oxide present in the molecule to the amount of the higher molecular weight alkylene oxide present in the molecule is in the range of between about 6:1 to 3:1, and in which the cloud point of said composition is greater than about 60° centigrade, wherein said glyphosate salt comprises the mono-iso-propylamine salt of N-phosphonomethyl glycine.

* * * * *